United States Patent [19]
Kifor et al.

[11] Patent Number: 5,958,884
[45] Date of Patent: Sep. 28, 1999

[54] COMPOSITIONS AND METHODS FOR TREATING ERECTILE DYSFUNCTION

[75] Inventors: Imre Kifor, Methuen; Gordon Williams, Belmont, both of Mass.

[73] Assignee: The Brigham and Women's Hospital, Inc., Boston, Mass.

[21] Appl. No.: 09/047,594

[22] Filed: Mar. 25, 1998

Related U.S. Application Data

[60] Provisional application No. 60/041,875, Apr. 11, 1997.
[51] Int. Cl.$^6$ .......................... A61K 31/41; A61K 31/70; A61K 38/08
[52] U.S. Cl. .............................. 514/16; 514/48; 514/381; 514/396; 514/397; 514/400
[58] Field of Search ................................ 514/16, 48, 381, 514/396, 397, 400; 530/316; 548/252, 253, 312.7, 323.1

[56] References Cited

U.S. PATENT DOCUMENTS

| | | | |
|---|---|---|---|
| 5,278,192 | 1/1994 | Fung et al. | 514/645 |
| 5,475,004 | 12/1995 | Heitsch et al. | 514/303 |
| 5,658,936 | 8/1997 | Kifor et al. | 514/381 |

FOREIGN PATENT DOCUMENTS

| | | |
|---|---|---|
| WO97/10821 | 3/1997 | WIPO. |
| PCT/US98/ 05886 | 6/1998 | WIPO. |
| PCT/US98/ 05893 | 8/1998 | WIPO. |

OTHER PUBLICATIONS

Andersson et al. Physiology of Penile Erection. Physiol. Reviews. vol. 75, No. 1, pp. 191–218, Jan. 1995.
Venegas, J., et al., "Assessment and modeling . . . ", *Modeling in Physiology,* H2109–2123 (1995).
Comiter, C., et al., "Urodynamic Risk Factors . . . ", *J. of Urology,* (1997), 158:181–185.
Braley, et al., "The Effects of Extra . . . ", Biochem. and Biophys. Res. Com., (1984), 123:2:810–815.
Price, et al., "Renin System Autonomy . . . ", 29th Annual Meeting, (1996), Abstract.
Price, et al., "The Paradox of the . . . ", 29th Annual Meeting, (1996), Abstract.
Price, et al., "Renal Perfusion is . . . ", 31st Annual Meeting, (1998), Abstract.
Persson, K., "Angiotensin II and Bladder . . . ", 1996, Abstract, *Amer. J. Physiol.* 271:5:1–2 R1186–1192.
Klinge, E., et al., "Comparative Study of Some Isolated Mammalian Smooth Muscle Effectors of Penile Erection", *ACTA, Physiol, Scand,* 1997, 100:354–367.
Croog, S., et al., "Sexual Symptoms in Hypertensive Patient", *Arch. Intern. Med.,* 1988, 148:788–794.
Clark, J., "A Possible Role for Angiotensin II in the Regulation of Male Sexual Behavior in Rats". *Physiology and Behavior,* 45:221–246 (1989).
Suzuki, H., et al., "Effects of First–Line Antihypertensive Agents on Sexual Function and Sex Hormones". *Journal of Hypertension,* 1988, 6(suppl 4): S649–S651.
Walley, T., et al., Adverse Effects of Captopril in Hospital Outpatients with Hypertension:, *Post Grad Med Journal,* 1990, 66:106–109.
Vickers, M., et al., "Angiotensin Production by Human Corporal Cavernosal Tissue". *The Journal of Urology,* 1992, 147:4, No. 100.
Haidle, G., et al., "Guidelines for Drug Treatment of Male Infertility", *Drugs,* 1:160–68 (1991).
Testa, M., et al., "Quality of Life and Antihypertensive Therapy in Men–A Comparison of Captopril with Enalapril". *The New England Journal of Medicine,* 1993, 328:907–913.
Goldstein, I., et al., "Impotence". *62nd Annual Meeting Program of the New England Section, American Urological Association, Inc—Session II,* 1993, pp. 64–65.
Joubert, P., et al., "The Effects of papervine, Prostaglandin E–1, and Phenylephrine on the Pulsatile Angiotensin II Secretion by Human Corporal Cavernosal Tissue", *Journal of Urology,* 1993 149:4:245A. No. 125.
Lopes–Martins, R., "Pharmacological Characterization of Rabbit Corpus Cavernosum Relaxation Mediated by the Tissue Kallikrein–kinin System", *Br. J. Pharmacol,* 1994, 113:81–86.
Prisant, L.M., et al., "Sexual Dysfunction with Antihypertensive Drugs". *Arch Intern Med,* 1994, 154:730–736.
Kifor, I., et al., "Tissue Angiotensin II and Impotence", *The Endocrine Society, 1995 Abstract Form,* Jan. 1995.
Andersson, K., et al., "Characterization of Immunoreactive . . . ", *J of Urology,* 1987, 137:1278–1282.

*Primary Examiner*—Jeffrey E. Russel
*Attorney, Agent, or Firm*—Wolf, Greenfield & Sacks, P.C.

[57] ABSTRACT

Methods and compositions for treating patients having erectile dysfunction are described. The method involves the step of treating a patient with a combination of an $AT_1$ specific Angiotensin II antagonist and Angiotensin II agonist. Preferably the $AT_1$ specific Angiotensin II antagonist is an $AT_1$ specific Angiotensin II antagonist. The composition is a pharmaceutical composition including an equivalent molecular ratio of an $AT_1$ specific Angiotensin II antagonist and Angiotensin II agonist.

13 Claims, No Drawings

SEQUENCE LISTING

<160> NUMBER OF SEQ ID NOS: 1

<210> SEQ ID NO 1
<211> LENGTH: 7
<212> TYPE: PRT
<213> ORGANISM: Homo sapiens

<400> SEQUENCE: 1

Asp Arg Val Tyr His Pro Phe
 1               5

COMPOSITIONS AND METHODS FOR TREATING ERECTILE DYSFUNCTION

This application claims the benefit of provisional application Ser. No. 60/041,875, filed Apr. 11, 1997.

BACKGROUND OF THE INVENTION

Erectile dysfunction, or impotence, is a common disorder that occurs in more than 10 million men in the USA. Although psychogenic etiology was thought to be the primary cause of erectile dysfunction, it now is believed that underlying organic diseases are responsible for most instances of erectile dysfunction. This conceptual change is supported by the particularly high incidence of impotence in men with essential hypertension, coronary artery disease and diabetes. In addition, a major mechanism responsible for impotence is an increase in the tone and/or contractility of smooth muscle within the corpus cavernosum penis and penile arteries that impede the modulation of penile blood flow by physiologic regulators. A similar mechanism, an increased tone and/or contractility of vascular smooth muscle, impedes the modulation of blood flow in the coronary, renal, and other arteries of hypertensive, diabetic etc. patients.

Other potential organic causes of erectile dysfunction include endocrine disorders, e.g., testicular failure and hyperprolactinemia; side effects of drugs, e.g., antiandrogens, antihypertensives, anticholinergics, antidepressants, antipsychotics, central nervous system depressants and drugs of habituation or addiction; penile diseases, e.g., Peyronie's disease, previous priapism, and penile trauma; neurological diseases, e.g., anterior temporal lobe lesions, diseases of the spinal cord, loss of sensory input, diseases of nervi erigentes, and diabetic autonomic neuropathy; and vascular diseases, e.g., essential hypertension, aortic occlusion, atherosclerotic occlusion or stenosis of the pudendal artery, venous leak, and diseases of the sinusoid spaces.

Disorders such as essential hypertension, coronary artery disease and diabetes involve an increase in vascular smooth muscle tone which imposes limitations on the modulation of regional blood flow in the kidney, heart, brain and other segments of the vascular bed. Clinical and experimental observations suggest that an imbalance between locally produced Angiotensin II and nitric oxide (NO) leads to an inappropriate tone of vascular smooth muscle resulting in increased blood pressure and altered regional blood flow. Indeed, administrations of nitric oxide synthase (NOS) inhibitors or Angiotensin II increase the tone and/or contractility of vascular smooth muscle and systemic blood pressure, thereby decreasing regional blood flow to organs such as the kidney and heart. Conversely, NO, Angiotensin II antagonists, renin inhibitors, and angiotensin converting enzyme (ACE) inhibitors decrease the smooth muscle tone and increase regional blood flow to these organs, and decrease systemic blood pressure.

As a modified vascular tissue, corpus cavernosum penis (ccp) produces and secretes the same range of autocrine and paracrine regulators as conventional vascular tissue. The smooth muscle tone of the ccp, however, does not appear to be regulated in the same manner as in the vascular wall. Presently it is postulated that the tone or contractility of ccp is modulated by adrenergic regulation and locally produced NO and endothelin. In the ccp, most studies have been directed to observing the relaxing effects of NO, vasoactive intestinal peptide (VIP), calcitonin gene-related peptide (CGRP) and parasympathetic innervation, which also have similar effects on conventional and ccp vascular smooth muscle.

Recently, it was discovered that renin-angiotensin system inhibitors, similar to the vascular tissue, the corpus cavernosum penis produces and secretes Angiotensin II, that plays an important role in modulation of the penile blood flow (PCT International Patent Application WO97/10821). Local, intracavemosal, or systemic administration of Angiotensin II antagonists or ACE inhibitors has a powerful effect on the penile blood flow. This effect can be used to improve erectile dysfunction without the inconvenience and side effects of drugs used for intracavernosal pharmacotherapy. Although the use of renin-angiotensin system inhibitors for treating impotence drastically improved the therapeutic options available to men experiencing impotence problems, it would be even more desirable to have an additional therapeutic method for treating impotence.

SUMMARY OF THE INVENTION

The invention involves the surprising finding that erectile dysfunction and other smooth muscle disorders can be treated by the administration of a combination of an $AT_1$ specific Angiotensin II antagonist and an Angiotensin II agonist. It was previously discovered that Angiotensin II antagonists are useful for inhibiting erectile dysfunction in a subject having erectile dysfunction and for improving erectile function in a normal subject (WO97/10821). Applicants have also recently discovered that Angiotensin II antagonists are useful for treating bladder dysfunction, hypertrophy and remodeling (co-pending application filed herewith). Angiotensin II antagonists inhibit the contraction of both penile and bladder smooth muscle. Prior to the present invention, however, it was not known that Angiotensin II agonists would potentiate the activity of $AT_1$ specific Angiotensin II antagonists when administered in conjunction with $AT_1$ specific Angiotensin II antagonists. This was surprising because agonists generally have the opposite effect of antagonists.

In one aspect the invention is a method for treating erectile dysfunction. The method involves the step of administering to a subject in need of such treatment, an $AT_1$ specific Angiotensin II antagonist and an Angiotensin II agonist in an amount effective to decrease the symptoms of erectile dysfunction. Preferably the subject is otherwise free of indications calling for $AT_1$ specific Angiotensin II antagonist and an Angiotensin II agonist treatment.

In one embodiment the $AT_1$ specific Angiotensin II antagonist is selected from the group consisting of Losartan, non-peptide Angiotensin II receptor antagonists, and polymorphic forms of Losartan. Preferably the angiotensin II inhibitor is Losartan. In another embodiment the Angiotensin II agonist is selected from the group consisting of p-aminophenylalanine6 angiotensin II, guanosine 15 5'-O-(3-thiotriphosphate,(6-biotinylamido)hexanoyl-Angiotensin II, dinitrophenyl-aminohexanoyl-Angiotensin II, [Hfv5] Angiotensin II, agonist analogues of angiotensin II including [Des-Asp1]heptapeptide and [Sar1]-derivatives, Angiotensin II, Asp-Arg-Val-Tyr-His-Pro-Phe (SEQ ID NO:1), and [Hcy3,5] Angiotensin II.

In another embodiment the effective amount is a dose which modifies acutely the systemic blood pressure of the subject by less than 5%. Preferably the effective amount is a dose which is sufficient to increase intracavemosal pressure to a level substantially the same as the mean arterial pressure.

The $AT_1$ specific Angiotensin II antagonist and an Angiotensin II agonist may be administered by any method known in the art. In one embodiment they are administered by intracavemosal injection, intraurethral device, or penile patches. Preferably they are administered orally.

According to another aspect of the invention a method of stimulating smooth muscle relaxation in smooth muscle expressing both the $AT_1$ and $AT_2$ receptors is provided. The method involves the step of contacting said smooth muscle expressing both the $AT_1$ and $AT_2$ receptors simultaneously with an $AT_1$ specific Angiotensin II antagonist and the Angiotensin II agonist in an amount effective to stimulate smooth muscle relaxation.

According to another aspect of the invention a pharmaceutical composition is provided. The pharmaceutical composition includes an $AT_1$ specific Angiotensin II antagonist, an Angiotensin II agonist, and a pharmaceutically acceptable carrier. In one embodiment the $AT_1$ specific Angiotensin II antagonist and the Angiotensin II agonist are present in equivalent molecular ratios. According to another embodiment the $AT_1$ specific Angiotensin II antagonist and the Angiotensin II agonist are present in a therapeutically amount effective for treating erectile dysfunction. In another embodiment the $AT_1$ specific Angiotensin II antagonist and the Angiotensin II agonist are present in a therapeutically amount effective for stimulating smooth muscle relaxation.

The invention is useful, inter alia, in subjects who are otherwise free of indications calling for treatment with a combination of $AT_1$ specific Angiotensin II antagonist and Angiotensin II agonist.

Each of the limitations of the invention can encompass various embodiments of the invention. It is, therefore, anticipated that each of the limitations of the invention involving any one element or combinations of elements can be included in each method.

DETAILED DESCRIPTION OF THE INVENTION

The invention is a composition and methods for treating erectile dysfunction and for stimulating smooth muscle relaxation. It was found according to the invention that a pharmaceutical combination of $AT_1$ specific Angiotensin II antagonists and Angiotensin II agonists causes smooth muscle relaxation in penile smooth muscle and other smooth muscle tissue such as the bladder. The effect seen with the combination of drugs is greater than that seen with an Angiotensin II antagonist alone. The effect is surprising because agonists which generally have an opposite effect than antagonists usually do not potentiate the effect of an antagonist.

Although Applicants do not wish to be bound by a particular mechanism it is believed that Angiotensin II agonists potentiate the effect of $AT_1$ specific Angiotensin II antagonists by their interactions with different Angiotensin II receptors. Angiotensin II is known to specifically interact with at least two cellular receptor subtypes $AT_1$ and $AT_2$.

The $AT_1$ receptor mediates the contractile effects of Angiotensin II and is involved in regulating the stimulation of regulatory peptide, growth factor and aldosterone secretion, cell proliferation, hypertrophy and secretion of extracellular matrix proteins. In the urinary bladder, the $AT_1$ receptor has a dominant role and when Angiotensin II is present, Angiotensin II interacts with the $AT_1$ receptor and causes smooth muscle contraction. Agonist binding to the G protein coupled $AT_1$ receptor activates PLC, and initiates a signal transduction pathway typical for G protein coupled receptors, with production of DAG and $IP_3$ The subsequent activation of PKC, mobilization of calcium from $IP_3$ sensitive intracellular stores, and the increased calcium influx through the L-type calcium channels promotes smooth muscle contraction in a manner similar to Angiotensin II. Specific Angiotensin II receptor antagonists such as Losartan suppress these effects.

The $AT_2$ receptors, however, are involved in mediation of smooth muscle relaxation and suppression of cell proliferation. The anti-growth effect of $AT_2$ receptors is mediated by inhibition of MAP kinase activity promoted by $AT_1$ receptors. When Angiotensin II or Angiotensin II agonists interact with $AT_2$ receptors the receptor is activated and promotes smooth muscle relaxation. Angiotensin II antagonists which interact with the $AT_2$ receptor inhibit the activation of the receptor and promote smooth muscle contraction.

The invention involves the finding that when both receptor subtypes are present in smooth muscle cells the balance between Angiotensin II, $AT_1$ specific Angiotensin II antagonists and Angiotensin II agonists can be manipulated to promote an enhanced stimulation of smooth muscle contraction through both sets of receptor subtypes. This is accomplished by using $AT_1$ specific Angiotensin II antagonists. When $AT_1$ specific Angiotensin II antagonists are added to smooth muscle cells expressing both $AT_1$ and $AT_2$ receptor subtypes, the AT specific Angiotensin II antagonists specifically interact with the $AT_1$ receptors leaving the majority of the $AT_2$ receptors available. The interaction between the $AT_1$ specific Angiotensin II antagonists and the $AT_1$ receptors promotes smooth muscle relaxation. Under normal conditions the free Angiotensin II would interact with the available $AT_2$ receptors and not the $AT_1$ receptors because the $AT_1$ receptors are involved in the interaction with the $AT_1$ specific angiotensin II antagonist. The interaction of Angiotensin II with $AT_1$ receptors also promotes smooth muscle relaxation. When Angiotensin II agonists are added with the $AT_1$ specific Angiotensin II antagonists, the agonists specifically interact with the available $AT_2$ receptors, similar to Angiotensin II, resulting in the promotion of smooth muscle relaxation. The effect of Angiotensin II agonists is stronger than that of Angiotensin II. Therefore, by administering $AT_1$ specific Angiotensin II antagonists and Angiotensin II agonists together smooth muscle relaxation is stimulated through two pathways and is enhanced with respect to smooth muscle relaxation which occurs as a result of stimulation with $AT_1$ specific Angiotensin II antagonists alone.

In one embodiment, the present invention relates to a method for treating a subject having symptoms of erectile dysfunction by administering to a subject an amount effective of an $AT_1$ specific Angiotensin II antagonist and Angiotensin II agonist to decrease the symptoms of erectile dysfunction. The $AT_1$ specific Angiotensin II antagonist and Angiotensin II agonist can be administered in an effective dose which does not reduce the systemic blood pressure within one day of administration by more than 10%. Acute lowering of systemic blood pressure by 10% or more is believed to cause sexual dysfunction, the opposite of the desired goal of the invention. It is preferred that the dose be low enough to cause an acute lowering of systemic blood pressure by no more than 5%. In one embodiment, the therapeutically effective dose is sufficient to increase intracavernosal pressure to a level substantially the same as the mean arterial pressure.

Erectile dysfunction is a disorder involving the failure of a male mammal to achieve erection, ejaculation, or both. Symptoms of erectile dysfunction include an inability to achieve or maintain an erection, ejaculatory failure, premature ejaculation, inability to achieve an orgasm. An increase in erectile dysfunction is often associated with age and is generally caused by a physical disease or as a side-effect of drug treatment.

The $AT_1$ specific Angiotensin II antagonist and Angiotensin II agonist is administered in an effective amount. An effective amount is one that is sufficient to achieve improvement in erectile function or an alleviation of the symptoms of erectile dysfunction.

An effective amount is that amount sufficient to produce a medically desirable result. Effective amounts will depend, of course, on the particular condition being treated; the severity of the condition, individual patient parameters including age, physical condition, size and weight, the duration of the treatment, the nature of the concurrent therapy (if any), the specific route of administration and like factors within the knowledge and expertise of the health practitioner. These factors are well known to those of ordinary skill in the art and can be addressed with no more than routine experimentation. For example, an amount effective for treating erectile dysfunction would be an amount sufficient to increase the intracavernosal pressure to a level substantially the same as the mean arterial pressure.

In one embodiment, the present invention relates to a method for stimulating smooth muscle relaxation by administering to a subject an effective amount of an $AT_1$ specific Angiotensin II antagonist and Angiotensin II agonist to stimulate smooth muscle relaxation. The $AT_1$ specific Angiotensin II antagonist and Angiotensin II agonist can be administered in an effective amount which does not reduce the systemic blood pressure within one day of administration by more than 10%. It is preferred that the amount be low enough to cause an acute lowering of systemic blood pressure by no more than 5%.

It is desirable to stimulate smooth muscle relaxation in subjects having smooth muscle contractile disorders. As used herein a smooth muscle contractile disorders is a disorder of the lung, gastrointestinal tract, cervix, bladder, vagina, or uterus arising as a result of excessive smooth muscle proliferation.

The $AT_1$ specific Angiotensin II antagonist and Angiotensin II agonist are administered in effective amounts. In one embodiment the effective amount is one that is sufficient to stimulate smooth muscle relaxation. In one embodiment the effective amount is an amount sufficient to prevent or reduce the risk of acquiring bladder hypertrophy and remodeling associated with bladder dysfunction. In another embodiment the effective amount is one that is sufficient to reduce the symptoms of bladder dysfunction. In yet another embodiment the effective amount is one that is sufficient to reduce the risk of acquiring the symptoms of bladder dysfunction.

For example, an amount effective for treating bladder dysfunction would be an amount sufficient to reduce the amount or activity of Angiotensin II in the bladder smooth muscle so as to lessen the contractile response of bladder smooth muscle to neural stimulation. Chronic is administration of the $AT_1$ specific Angiotensin II antagonist and Angiotensin II agonist of the invention will prevent or reduce the risk of acquiring an increased contractile response such as that associated with high sodium intake, suppression of NOS activity, and partial outlet obstruction. Thus, it will be understood that the $AT_1$ specific Angiotensin II antagonist and Angiotensin II agonist of the invention can be used to treat bladder dysfunction prophylactically in subjects at risk of developing bladder dysfunction as well as in subjects exhibiting symptoms of bladder dysfunction and subjects having bladder hypertrophy and remodeling.

A "subject exhibiting symptoms of bladder dysfunction" is a subject who has a disorder involving abnormalities of bladder detrusor smooth muscle arising from overproduction of Angiotensin II or bladder hypertrophy and remodeling. Symptoms of bladder dysfunction include but are not limited to dysuria, frequency and urgency, incontinence, enuresis and complete loss of bladder function. The abnormalities of bladder smooth muscle may arise as a result of disease, chemicals, radiation, foreign bodies, (catheters and stones), and infiltration of the muscles by tumors of the bladder or may be simply due to advancement of age.

A "subject at risk of developing bladder dysfunction" is a subject who has a propensity of developing bladder dysfunction because of certain factors affecting the bladder of the subject. Factors which influence the development of bladder dysfunction include but are not limited to exposure to infectious agents, chemicals, radiation or foreign bodies, a predisposition to develop tumors of the bladder or adjacent organs and age. It is desirable to reduce the risk in these subjects of developing bladder dysfunction. Reducing the risk of bladder dysfunction includes a slowing of the progression towards bladder dysfunction or preventing the development of bladder dysfunction.

The term "subject" as used herein, is intended to mean humans, primates, horses, cows, swine, goats, sheep, dogs, and cats.

In one embodiment, the subjects treated by the methods of the present invention are otherwise free of indications for a combination of $AT_1$ specific Angiotensin II antagonist and Angiotensin II agonist. By "free of indications", it is meant that the subject does not have indications (e.g., symptoms or a clinical history) which, prior to the present invention, were treated with an $AT_1$ specific Angiotensin II antagonist and Angiotensin II agonist.

The $AT_1$ specific Angiotensin II antagonist and Angiotensin II agonist of the invention are administered in effective amounts. Generally, systemic doses of active compounds will be from about 0.01 milligrams/kg body weight per day to 10 milligrams/kg body weight per day. It is expected that oral doses in the range of 0.1 to 100 milligrams/kg body weight, in one or several administrations per day, will yield the desired results. In the event that the response in a subject is insufficient at such doses, even higher doses (or effective higher doses by a different, more localized delivery route) may be employed to the extent that patient tolerance permits. In the event that lower doses are sufficient to improve the condition being treated lower doses may be employed. Multiple doses per day are contemplated to achieve appropriate systemic levels of compounds. In one embodiment a maximal dose is administered first, followed by submaximal dosages. An effective amount is less than that which will have the effect of acutely modifying the systemic blood pressure by greater than 10%. It preferably is so low so as to acutely modify systemic blood pressure by no more than 5% and can be even so low so as to have no measurable acute effect on systemic blood pressure.

The invention also includes pharmaceutical compositions. The pharmaceutical composition includes an $AT_1$ specific Angiotensin II antagonist, an Angiotensin II agonist, and a pharmaceutically acceptable carrier.

The $AT_1$ specific Angiotensin II antagonist and the Angiotensin II agonist preferably are present in the composition in equivalent molecular ratios. The term "equivalent molecular ratios" as used herein means that the active agents in the composition have substantially equivalent numbers of molecules. The ratio of the active agents is dependent on the molecular weight of the active agents rather than the actual weight of the active agents.

In one embodiment the $AT_1$ specific Angiotensin II antagonist and the Angiotensin II agonist are present in an effective dose for treating erectile dysfunction. In another embodiment the $AT_1$ specific Angiotensin II antagonist and the Angiotensin II agonist are present in an effective dose for stimulating smooth muscle relaxation.

$AT_1$ specific Angiotensin II antagonists are compounds which interfere with the activity of Angiotensin II by binding to $AT_1$ Angiotensin II receptors and interfering with its activity. $AT_1$ specific Angiotensin II antagonists are well known and include peptide compounds and non-peptide compounds. Most $AT_1$ specific Angiotensin II antagonists are slightly modified congeners in which agonist activity is attenuated by replacement of phenylalanine in position 8 with some other amino acid; stability can be enhanced by other replacements that slow degeneration in vivo. Examples of $AT_1$ specific Angiotensin II antagonists include but are not limited to: Losartan (DUP753/MK954, DuPont Merck Pharmaceutical Company, U.S. Pat. No. 5,138,069 and EPO 0,253,310 (published Jan. 20, 1988) and EPO 0,324,377 (published Jul. 19, 1989); non-peptide Angiotensin II receptor antagonists (U.S. Pat. No. 5,264,581); polymorphic forms of Losartan (U.S. Pat. No. 5,608,075).

$AT_1$ specific Angiotensin II antagonists of the invention are those which specifically interact with the $AT_1$ receptor subtype. They are well known in the art. Whether an angiotensin II antagonist specifically interacts with $AT_1$ can be determined using any of a number of art recognized assays. For example, whether an angiotensin II antagonist specifically interacts with $AT_1$ can be determined using the assay disclosed in U.S. Pat. No. 5,554,624, which is hereby incorporated by reference. Briefly, the assay involves the following:

A membrane fraction used in the assay is prepared from rat adrenal glands. The tissues are collected in 50 mM Tris-HCl buffer, pH 7.5, so that the concentration is 20% (w/v) and are homogenized at 1000×rpm. The homogenate is centrifuged at 1000 g for 10 min and the supernatant further centrifuged at 100,000 g for 1 h. The resulting membrane pellet is then resuspended in the above buffer at a concentration of 10 mg of protein/mL. 100 mu L aliquots of the membrane suspension can be stored frozen at −70° C. until used.

Aliquots containing 15 mu g of protein are incubated at 25° C. for 1 h in incubation buffer containing (final concentrations): NaCl (120 mM), $Mg_2$ (5 mM), 0.05% bovine serum albumin, and Tris (50 mM), adjusted to pH 7.5, with or without dithiothreitol (1 mM) to characterize whether drugs preferentially interact with $AT_1$ or $AT_2$ receptor subtypes. Incubation is initiated by the addition of 10 nM 3H-Angiotensin II. Total incubation volume is 250 mu L. Nonspecific binding is measured by incubation in the presence of 0.1 mu M Sar<1>Ile<8>-Angiotensin II. Test compounds are studied in the range of concentrations 10<−10>M−10<> <5>M. Binding is terminated by rapid filtration using a Millipore Multiscreen device. Filters are washed three times with 250 mu L of the corresponding buffer in the presence or absence of 1 mM dithiothreitol. Dry filters are placed into vials containing 3 mL of scintillation fluid and the radioactivity counted in a scintillation counter. The $IC_{50}$ value (concentration for 50% displacement of the specifically bound 3H-angiotensin II) is determined for each test compound.

The Angiotensin II agonists of the invention may specifically interact with both of the $AT_1$ and $AT_2$ receptor subtypes. Optionally the Angiotensin II agonist may specifically interact with the $AT_2$ receptor. Angiotensin II agonists include but are not limited to p-aminophenylalanine6 angiotensin II (Speth et al. *Biochem Biophys Res Commun* 169 (3), p. 997–1006 (1990)); guanosine 15 5'-O-(3-thiotriphosphate (Speth et al. *Biochem Biophys Res Commun* 169 (3), p. 997–1006 (1990)); (6-biotinylamido)hexanoyl-Angiotensin II (Bonnafous et al., *J. Recept Res.,* v. 8 (1–4), p. 295–309 (1988)); dinitrophenyl-aminohexanoyl-Angiotensin II (Bonnafous et al, *J Recept Res.,* v. 8 (1–4), p. 295–309 (1988)); [Hfv5]Angiotensin II (Vine et al., *J. Med Chem,* v. 24 (9), p. 1043–1047 (1981)); agonist analogues of angiotensin II including [Des-Asp1]heptapeptide and [Sar1]-derivatives (Saltman et al., *Endocrinology,* v. 97, p. 275–282 (1975)); Angiotensin II, Asp-Arg-Val-Tyr-His-Pro-Phe and other agonists disclosed (Plucinska et al., *J. Med. Chem,* v. 36, p. 1902–1913 (1993)); and [Hcy3,5] Angiotensin II (Spear et al., J. Med Chem, v. 33, p. 1935–1940 (1990).

The $AT_1$ specific Angiotensin II antagonists and Angiotensin II agonists described herein are commercially available compounds, are derived from commercially available compounds or are synthesized de novo using routine chemical synthetic procedures known to those of ordinary skill in the art.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. As used herein, a composition of an $AT_1$ specific Angiotensin II antagonist and Angiotensin II agonist means the compounds described above as well as salts thereof.

The $AT_1$ specific Angiotensin II antagonist and Angiotensin II agonist may be combined, optionally, with a pharmaceutically-acceptable carrier. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the $AT_1$ specific Angiotensin II antagonist and Angiotensin II agonist, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the $AT_1$ specific Angiotensin II antagonist and Angiotensin II agonist into association with a carrier which constitutes one or more accessory ingredients. In general, the compositions are prepared by uniformly and intimately bringing the $AT_1$ specific Angiotensin II antagonist and Angiotensin II agonist into association with a liquid carrier, a finely divided solid carrier, or both, and then, if necessary, shaping the product.

Compositions suitable for oral administration may be presented as discrete units, such as capsules, tablets, lozenges, each containing a predetermined amount of the $AT_1$ specific Angiotensin II antagonist and Angiotensin II agonist. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the $AT_1$ specific Angiotensin II antagonist and Angiotensin II agonist described above, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the $AT_1$ specific Angiotensin II antagonist and Angiotensin II agonist is contained in a form within a matrix such as those described in U.S. Pat. Nos. 4,452,775, 4,667,014, 4,748,034 and 5,239,660 and (b) difusional systems in which an active component permeates at a controlled rate from a polymer such as described in U.S. Pat. Nos. 3,832, 253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Each of the foregoing patents, patent applications and references is incorporated by reference in its entirety herein by reference. It should be understood that various changes and modification of the embodiment described above may be made within the scope of this invention. Thus, it is intended that all matter contained in the above description shall be interpreted in an illustrative and not limiting sense.

What we claim is:

1. A method for treating erectile dysfunction in a subject comprising:

administering to a subject in need of such treatment, an effective amount of an $AT_1$ specific Angiotensin II antagonist and an Angiotensin II agonist to decrease the symptoms of erectile dysfunction.

2. A method for treating erectile dysfunction as claimed in claim 1, wherein the $AT_1$ specific Angiotensin II antagonist is selected from the group consisting of Losartan, non-peptide Angiotensin II receptor antagonists, and polymorphic forms of Losartan.

3. A method for treating erectile dysfunction as claimed in claim 2, wherein the Angiotensin II agonist is selected from the group consisting of p-aminophenylalanine6 angiotensin II, guanosine 5'-O-(3-thiotriphosphate) (6-biotinylamido) hexanoyl-Angiotensin II, dinitrophenyl-aminohexanoyl-Angiotensin II, [Hfv5]Angiotensin II, [Des-Asp1] Angiotensin II, [Sar1]Angiotensin II Angiotensin II, Asp-Arg-Val-Tyr-His-Pro-Phe (SEQ ID NO:1), and [Hcy3,5] Angiotensin II.

4. A method for treating erectile dysfunction as claimed in claim 2, wherein the angiotensin II antagonist is Losartan.

5. A method for treating erectile dysfunction as claimed in claim 1, wherein the effective amount is a dose which modifies acutely the systemic blood pressure of the subject by less than 5%.

6. A method for treating erectile dysfunction as claimed in claim 1, wherein the $AT_1$ specific Angiotensin II antagonist and an Angiotensin II agonist are administered by intracavernosal injection, intraurethral device, or penile patches.

7. A method for treating erectile dysfunction as claimed in claim 1, wherein the subject is otherwise free of indications calling for $AT_1$ specific Angiotensin II antagonist and an Angiotensin II agonist treatment.

8. A method for treating erectile dysfunction as claimed in claim 1, wherein the $AT_1$ specific Angiotensin II antagonist and an Angiotensin II agonist are administered orally.

9. A method for treating erectile dysfunction as claimed in claim 1 wherein the effective amount is a dose which is sufficient to increase intracavernosal pressure to a level substantially the same as the mean arterial pressure.

10. A pharmaceutical composition, comprising:

an $AT_1$ specific Angiotensin II antagonist, an Angiotensin II agonist, and a pharmaceutically acceptable carrier.

11. The pharmaceutical composition of claim 10, wherein the $AT_1$ specific Angiotensin II antagonist and the Angiotensin II agonist are present in equivalent molecular ratios.

12. The pharmaceutical composition of claim 10, wherein the $AT_1$ specific Angiotensin II antagonist and the Angiotensin II agonist are present in an effective dose for treating erectile dysfunction.

13. The pharmaceutical composition of claim 10, wherein the $AT_1$ specific Angiotensin II antagonist and the Angiotensin II agonist are present in an effective dose for treating bladder dysfunction.

* * * * *